(12) United States Patent
Rhee et al.

(10) Patent No.: US 8,835,164 B2
(45) Date of Patent: Sep. 16, 2014

(54) CELL LINE STABLY EXPRESSING MUTATED ONCOPROTEIN E6 AND METHOD OF SCREENING ANTICANCER COMPOUND OF UTERINE CERVICAL CANCER USING THE SAME

(75) Inventors: Jee Eun Rhee, Seoul (KR); Dae Ho Jang, Seoul (KR); Sung Soon Kim, Seoul (KR); Byeong Sun Choi, Gyeonggi-Do (KR)

(73) Assignee: Korea Center for Disease Control and Prevention, Chungcheongbuk-do (KR)

( * ) Notice: Subject to any disclaimer, the term of this patent is extended or adjusted under 35 U.S.C. 154(b) by 749 days.

(21) Appl. No.: 12/795,211

(22) Filed: Jun. 7, 2010

(65) Prior Publication Data
US 2011/0081644 A1 Apr. 7, 2011

(30) Foreign Application Priority Data
Oct. 1, 2009 (KR) .................. 10-2009-0093814

(51) Int. Cl.
| | |
|---|---|
| C12N 5/00 | (2006.01) |
| C12Q 1/37 | (2006.01) |
| C12N 5/07 | (2010.01) |
| C12N 15/09 | (2006.01) |
| G01N 33/50 | (2006.01) |
| A61K 33/24 | (2006.01) |
| A61K 31/353 | (2006.01) |

(52) U.S. Cl.
CPC ............ *G01N 33/5011* (2013.01); *A61K 33/24* (2013.01); *A61K 31/353* (2013.01)
USPC ...................... 435/325; 435/320.1; 435/23.72; 435/367; 435/69.3

(58) Field of Classification Search
CPC ..... C12N 15/67; A61K 31/353; A61K 33/24; A61K 36/11
USPC .......................................... 435/235
See application file for complete search history.

(56) References Cited

FOREIGN PATENT DOCUMENTS
WO WO2004098526 * 11/2004

OTHER PUBLICATIONS

Yim et al., Genomic and Proteomic Expression Patterns in HPV-16 E6 Gene Transfected Stable Human Carcinoma Cell Lines, 2004, DNA and Cell Biology, 23(12):826-835.*
GenBank accession No. NC_001526, direct submission Aug. 1, 2000, National Center for Biotechnology Information, NIH.*
Evans et al., HLA-A2-restricted peripheral blood cytolytic T lymphocyte response to HPV type 16 proteins E6 and E7 from patients with neoplastic cervical lesions, Cancer Immunol Immunother, 1996, 42:151-160.*
Min, Sang-Kee, et al.; "Intratypic Variants of HPY-16 E6/E7 Oncogene Isolated from Sexually High-Risk Women in Busan".; Journal of Life Science 2009, vol. 19, No. 6; pp. 765-769.
GenBank AAL96604.1, published Aug. 12, 2001 (1 page).
Matsumoto, K. et al., "Human Papillomavirus Type 16 E6 Variants and HLA Class II Alleles Among Japanese Women with Cervical Cancer", Int. J. Cancer: 106, pp. 919-922 (2003).
Korean Office Action for Korean Application No. 10-2009-0093814, dated Jun. 14, 2011.

\* cited by examiner

*Primary Examiner* — Zachariah Lucas
*Assistant Examiner* — Barry A Chestnut
(74) *Attorney, Agent, or Firm* — Edwards Wildman Palmer LLP; Kongsik Kim (57) ABSTRACT

Disclosed are a cell line that expresses protein of Seq. No. 1, and a method for screening an anticancer compound of uterine cervical cancer by using the same. The stable cell line that expresses oncoprotein E6 of a human papillomavirus type 16 variant strain is used to determine a difference in amounts of expression of tumor suppressor genes, such as p53, between E6 protein of the reference strain and E6 protein of a variant strain, thereby screening an anticancer compound of uterine cervical cancer, etc. Further, it is possible to develop an anticancer agent of uterine cervical cancer.

4 Claims, 4 Drawing Sheets

<10⁻⁶ plate>

CELL LINE STABLY EXPRESSING MUTATED ONCOPROTEIN E6 AND METHOD OF SCREENING ANTICANCER COMPOUND OF UTERINE CERVICAL CANCER USING THE SAME

CROSS-REFERENCE TO RELATED APPLICATION

This application claims under 35 U.S.C. §119(a) the benefit of Korean Application No. 10-2009-0093814 filed Oct. 1, 2009, the entire contents of which are incorporated herein by reference.

BACKGROUND OF THE INVENTION

1. Field of the Invention

The present invention relates to a cell line expressing oncoprotein E6 of a human papillomavirus type 16 variant strain, and a method of screening an anticancer compound of uterine cervical cancer using the same.

2. Description of the Prior Art

Human papillomavirus (HPV) is a main cause of infection of the genital tract and also causes malignant tumors resulting from oral infection in the skin or oral cavity (Zhebe et al., 1997; Chrisofos et al., 2004). Infection of the genital tract caused by HPV is one of the most common diseases transmitted by sexual contact in both males and females all over the world. Recently, it is one of the most frequently appearing diseases (Ho et al., 1998; Jung et al., 2004). Generation of cancer cells appearing in the uterine cervix is caused mostly by HPV and at least about 120 genotypes of HPV have been known to date. Such a lot of genotypes of HPV may be classified into three types, i.e., the high-risk group, the intermediate-risk group and the low-risk group, depending on the risk of tumors caused by the corresponding type of HPV. Particularly, it is reported that HPV 16, 18 and 31 genotypes of the high-risk group are most highly related to uterine cervical cancer and tumor genesis (zur Hausen., 1996; Koutsky et al., 1997; Munoz et al., 2002; Scheurer et al., 2005).

HPV is a subgroup of papovavirus, is a small non-enveloped virus, and has two kinds of proteins participating in host cell infection and cell cycle. One kind of such proteins is a protein that acts in the initial stage of host cell infection and the other is a protein that controls the cell cycle of the virus in the late stage of host cell infection. Among such proteins, E6 protein that acts in the initial stage plays an important role in the duplication of viral genetic materials and tumor genesis in the host cells. Basically, HPV infection is initiated by damages of epithelial cells. Damages of the basal layer of epithelial cells cause the genetic materials of HPV to start the duplication cycle, which is initiated by the interaction between the materials of host cells and the long control region (LCR) positioned at HPV genomes. Such interaction leads the duplication of E6 and E7 protein genes. These proteins are oncoproteins, and perform their functions as tumor proteins by disturbing the growth factor control path of the host cells through the inactivation or decomposition of p53 or pRb, which is a tumor suppressor gene of the host cells, or by controlling the host cell environment so as to facilitate the duplication of viral genetic materials (Jung et al., 2004). It is known to date that HPV16 and 18 classified as the high-risk HPV genotype are inserted into the infected host cell to cause tumors, in which the interaction between E6 oncoprotein and p53, which is a host tumor suppressor factor, causes uterine cervical cancer (Kiyono et al., 1998; zur Hausen., 1999; Furumoto et al., 2002). It is also known that HPV16 and 18 participate in the immortalization of human epithelial cells together with hTERT (human telomerase reverse transcriptase) (Munger & Howley, 2002).

Meanwhile, it is observed through the study about the HIV infection rate in a domestic high-risk female group and about variant strains that the HIV infection rate is 47% in the domestic high-risk female group and the HPV16 genotype is the most predominant type and occupies 35% of the infection (Choi et al. 2003). After the base sequence of the E6 oncogene is analyzed, it is also observed that 68% thereof are variants (Choi et al., 2007). According to many epidemiologic studies, it is known that HPV16 variant strains affect continuous viral infection and uterine dysplasia resulting therefrom (Berumen et al., 2001, del Refugio Gonzales-Losa et al., 2004; Grodzki et al., 2006; Hildesheim et al., 2001; Lee et al., 2008; Londesborough et al., 1996; Picconi et al., 2003; Sathish et al., 2005; Sichero et al., 2007; Villa et al., 2000; Xi et al., 1995, 1997, 2006). However, there is no sufficient study about the mechanism of generation of uterine cervical cancer caused by such variant strains not only in Korea but also in other countries. After the study of HPV16 E6 L83V (Charkrabarti et al., 2004), it is the only reported result that such variant strains cause uterine cervical cancer in a manner different from the reference strain by activating mitogen-activated protein kinase (MAPK). Recently, active studies have been conducted by many research workers.

SUMMARY OF THE INVENTION

Accordingly, the present invention has been made to solve the above-mentioned problems occurring in the prior art, and the present invention provides a method of screening an anticancer compound of uterine cervical cancer caused by a variant strain in domestic populations by screening in vivo proteins participating in the generation of uterine cervical cancer caused by a HPV16 variant strain, which is a domestic popular strain, through the construction of a cell line in which an oncoprotein of a HPV16 variant strain is expressed, and by investigating an interrelation of biomolecular control between the oncogene and the characterized protein.

An object of the present invention is to provide a cell line expressing oncoprotein E6 of a human papillomavirus type 16 variant strain.

Another object of the present invention is to provide a method of screening an anticancer compound by using the above cell line.

In one aspect, the present invention provides a cell line expressing a protein represented by Seq. No. 1 to achieve the above objects. The cell line includes genes encoding the protein represented by Seq. No. 1. In addition, the genes are obtained by carrying out PCR (polymerase chain reaction) with the primers represented by Seq. Nos. 2 and 3 according to a preferred embodiment of the present invention.

The inventors of the present invention have deposited a stable 16 cell line expressing oncoprotein E6 of a human papillomavirus type variant strain constructed in accordance with the present invention to Korean Cell Line Research Foundation (KCLRF) [Address: Cancer Research Institute, Seoul National University, College of Medicine, 28 Yongon-dong, Chongno-gu, Seoul, 110-744, KOREA] (Deposited Strain Name: HOE6V, Deposition No. KCLRF-BP-00218, deposited on Sep. 28, 2009). All restrictions upon public access to the deposited material will be irrevocably removed upon the grant of a patent on this application.

In another aspect, the present invention provides a method of screening an anticancer compound of uterine cervical cancer by using the above cell line. In accordance with a preferred embodiment of the present invention, the method may include a step of determining a difference in expression amount of p53 between E6 protein of the human papillomavirus type 16 reference strain and that of a variant strain.

The stable cell line expressing oncoprotein E6 of a human papillomavirus (HPV) type 16 variant strain constructed according to the present invention may be used to determine a difference in expression amount of tumor suppressor genes, such as p53, between E6 protein of the human papillomavirus type 16 reference strain and that of a variant strain. In this manner, it is possible to screen an anticancer compound of uterine cervical cancer. Further, it is possible to develop an anticancer agent of uterine cervical cancer.

BRIEF DESCRIPTION OF THE DRAWINGS

The above and other objects, features and advantages of the present invention will be more apparent from the following detailed description taken in conjunction with the accompanying drawings, in which:

FIG. 4 shows the results of aligning the E6 DNA sequence of the HPV16 E6 reference strain (A) of pDH085 (SEQ ID NO: 5) and that of the HPV16 E6 variant strain (B) of pDH086 (SEQ ID NO: 6) with the sequences of the HPV16 reference strain (SEQ ID NO: 7) and variant strain (SEQ ID NO: 8) updated in NCBI, wherein the red box represents the position of a mutation site (B: the $96^{th}$ T→G);

DETAILED DESCRIPTION OF THE EXEMPLARY EMBODIMENTS

Although an exemplary embodiment of the present invention has been described for illustrative purposes, those skilled in the art will appreciate that various modifications, additions and substitutions are possible, without departing from the scope and spirit of the invention as disclosed in the accompanying claims.

EXAMPLES

Example 1

Acquisition of Oncogene E6 from HPV16 Reference Strain and Variant Strain and Cloning Thereof into TA® Vector 1-1. Acquisition of Oncogene from HPV16 Reference Strain and Variant Strain DNAs are extracted from the samples identified as the HPV16 reference strain and variant strain through the local based service by using a QiAmp® Blood minikit. The amount of DNA extracted from each sample is measured by using an Invitrogen Qubit. Then, PCR is carried out by using E6-081 (Seq. No. 2)/E6-082 (Seq. No. 3) primer set in the presence of 100 μg of DNA as a template for 30 cycles under the conditions of 94° C., 1 minute; 60° C., 1 minute; and 72° C., 1.5 minutes.

TABLE 1

Primers Used in Examples

| Seq. No. | Primer | Direction | Sequence | Position |
|---|---|---|---|---|
| 2 | E6-081 | Forward | 5'-GTTATGGTTATGCACC AAAAGAGAACTGCAATG-3' | E6 |
| 3 | E6-082 | Reverse | 5'-GGCAGCTGGGTTTCTCT ACGTGTTC-3' | E6 |
| 4 | E6-083 | Forward | 5'-CCGTTGTGTGATTTGTT AATTAGGTG-3' | E6 |

Figure 1:
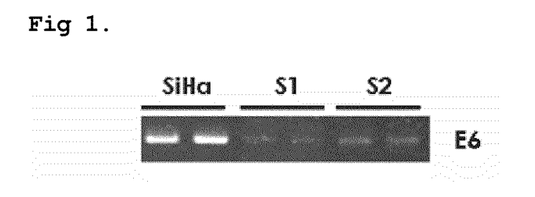
FIG. 1 shows the results of running E6 gene products amplified by PCR from the HPV16 E6 reference strain and a variant strain thereof through an agarose gel, wherein S1 represents oncogene E6 of the reference strain, S2 represents oncogene E6 of the variant strain, S represents a sample infected with HPV, and SiHa is a positive control.

Electrophoresis is carried out on 2% agarose gel to determine the size of the PCR products, and the DNA is washed by using a QiAmp® PCR clean up kit for the purpose of cloning into a TA® vector. After the PCR, E6 genes are amplified as shown in FIG. 1. After the DNA obtained as described above is sequenced, it can be seen that the samples infected with HPV16 include the reference strain having no mutation on the E6 sequence and the variant strain having D25E mutation (aspartic acid (D), the $25^{th}$ amino acid of E6 protein, is substituted with glutamic acid (E)).

1-1. Cloning into PCR2.1-TOPO® Vector

The DNA prepared as described above is mixed with 4 μl of the PCR product, 1 μl of saline and 1 μl of TOPO® enzyme, and then is subjected to ligation, according to the producer's manual. After incubating the DNA at room temperature for 3 hours, the DNA is transformed to competent cells. After the transformation, the cells are applied to an LB medium containing an antibiotic and X-gal and incubated at 37° C. overnight, and then only the white colony is selected.

1-2. Determination of Cloning

Figure 2:
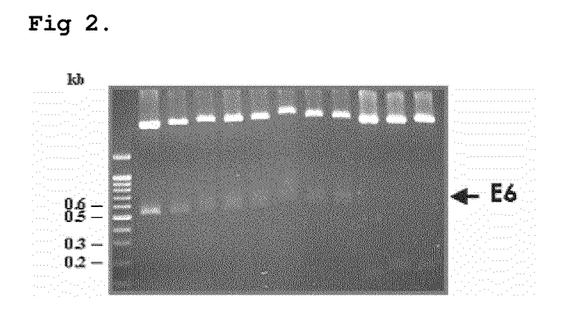
FIG. 2 shows the results of running HPV16 E6 cloned into a TA® vector through an agarose gel, after digesting it with EcoRI.

The selected colony is cultured in LB broth overnight, DNA is extracted by using a QIAGEN® mini prep. kit and the concentration thereof is determined. Then, EcoRI restriction enzyme is used to digest 1 μg of DNA at 37° C. for 1 hour, followed by agarose gel running, to determine whether the exact E6 genes are cloned or not. After the determination, DNA bands are observed with the size corresponding to E6 oncogene obtained from the reference strain and the variant strain (see FIG. 2), and thus the exactly cloned colony can be identified. After the determination of cloning, DNA sequencing analysis is carried out for the identified constructs to ascertain the base sequences. In this manner, it is possible to obtain constructs including exact E6 genes cloned into the TA® vector, and the constructs are designated as pDH081 and pDH082 (see Table 2).

Example 2

Cloning of Oncogene E6 from HPV16 Reference Strain and Variant Strain into Lentivirus Vector 2-1. Acquisition of Insert DNA for Cloning into Lentivirus Vector The construct that is shown to include the oncogene of the HPV16 reference strain and variant strain cloned into the TA® vector is taken as a template and E6-081/E6-082 primer set is used to carry out PCR for 30 cycles under the conditions of 94° C., 1 minute; 60° C., 1 minute; and 72° C., 1.5 minutes. Then, electrophoresis is carried out on 2% agarose gel to determine the size of the PCR product, and the DNA is washed by using a QiAmp® PCR clean up kit so that it may be used as an insert for the cloning into a lentivirus vector.

2-2. Cloning into pLenti6.5/V5-TOPO® Vector

The DNA prepared as described above is subjected to ligation according to the producer's manual (Invitrogen™). After the DNA is incubated at room temperature for 3 hours, it is transformed into competent cells. The transformed cells are applied to an LB medium containing an antibiotic, followed by culture in an incubator at 37° C. overnight.

2-3. Determination of Cloning

Figure 3:
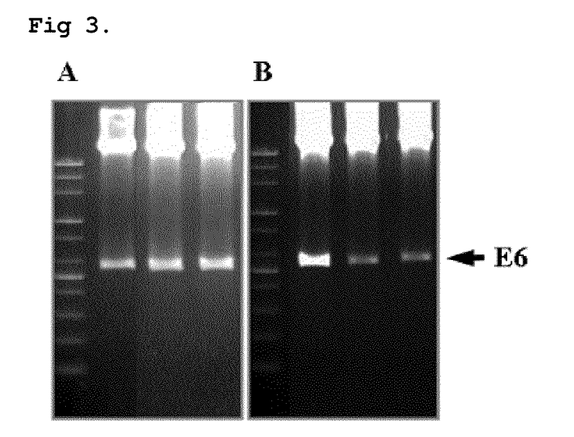
FIG. 3 shows the results of running the reference strain (A) and the variant strain (B) of HPV16 E6 cloned into a lentivirus vector through an agarose gel, after the dual digestion with BamHI and PstI.

The resultant colony is cultured in LB broth overnight, the DNA is extracted by using a QIAGEN® mini prep. kit and the concentration is determined. Then, BamHI and EcoRI restriction enzymes are used to digest 1 μg of DNA at 37° C. for 1 hour, followed by agarose gel running, to determine whether the DNA band with a predetermined size is observed or not. After the determination, a DNA band of E6 is observed with a size of about 0.6 kb (see FIG. 3). After the determination of cloning, DNA sequencing analysis is carried out for the identified constructs to ascertain the base sequences and the gene direction (see FIG. 4). In this manner, it is possible to obtain constructs including E6 genes cloned into the lentivirus vector, and the constructs are designated as pDH085 and pDH086 (see Table 2).

TABLE 2

Plasmids used in Examples

| Plasmid | Characteristics | Reference |
|---|---|---|
| pCR2.1-TOPO | PCR product cloning vector; $Ap^r$ | Invitrogen |
| pLenti6.3/V5-TOPO | Lentivirus system expressing protein in divided and non-divided mammal cells; $Ap^r$, $Blsticidin^r$ | Invitrogen |
| pDH081 | pCR2.1-TOPO® containing reference strain E6; $Ap^r$ | Inventive Example |
| pDH082 | pCR2.1-TOPO® containing variant strain E6; $Ap^r$ | Inventive Example |
| pDH085 | pLenti6.3/V5-TOPO® containing reference strain E6; $Ap^r$ | Inventive Example |
| pDH086 | pLenti6.3/V5-TOPO® containing variant strain E6; $Ap^r$ | Inventive Example |

* $Ap^r$: ampicilin resistance

Example 3

Production of Lentivirus with Target Protein 3-1. Production of Lentivirus

For the transfection of 293FT cells, a PureLink® HiPure Plasmid DNA Purification kit (Invitrogen™) is used to extract a large amount of plasmids of the construct including the oncogene cloned into the lentivirus vector. To the cells frozen in 293FT cell culture-75T flask, a medium containing 25 ml of DMEM, 10% FBS, 1% penicillin-streptomycin and 5% MEM non-essential amino acid is added. Then, the cells are cultured in a $CO_2$ incubator until an adequate amount of cells (about $1 \times 10^8$) are obtained. To produce the lentivirus, 9 μg of ViraPower™ Packaging Mix, 3 μg of pLenti expressing plasmid DNA and 36 μl of Lipofectamine™ 2000 are mixed, and then the DNA-Lipofectamine™ 2000 complex is added to the 293FT cells prepared as described above. A virus-containing supernatant is obtained 48 hours after the transfection and the stock is stored at −80° C.

3-2. Determination of Titer of Produced Lentivirus

Figure 5:
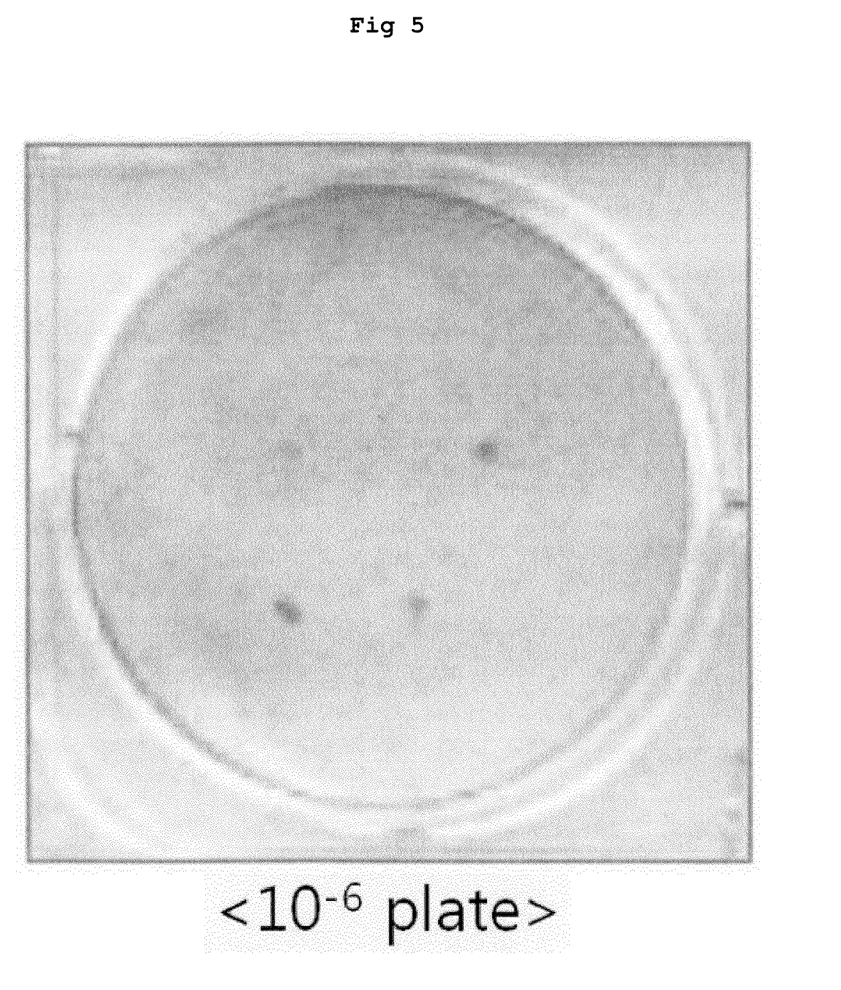
FIG. 5 shows the results of virus titer determination using the crystal violet staining of a blasticidin-resistant colony diluted to $1:10^6$, wherein the virus titer is $4 \times 10^6$ TU/ml.

To determine the titer of the lentivirus, C33A cells are cultured in a 6-well plate to a cell count of $2 \times 10^5$. The lentivirus stock is provided as serial dilutions from $10^{-2}$ to $10^{-6}$ and added to the plate prepared as described above. Then, polybrene is added to each well in an amount of 6 μg/ml, and the cells are cultured in a culture medium containing balsticidin (10 μg/ml) in a 37° C., 5% $CO_2$ incubator. After 10 days, the culture medium is removed and 1 ml of crystal violet solution is added and the temperature is maintained at room temperature for 10 minutes. Then, blue stained colonies are counted to determine the virus titer. As a result, it can be seen that $4 \times 10^6$ TU/ml of virus stock is obtained (FIG. 5). Such a titer suggests that the virus is obtained in an amount adequate to construct a stable cell line and above $1 \times 10^5$ TU/ml (virus titer recommended by the producer's manual).

Example 4

Construction of Stable Cell Line Containing Oncogene

Figure 6:
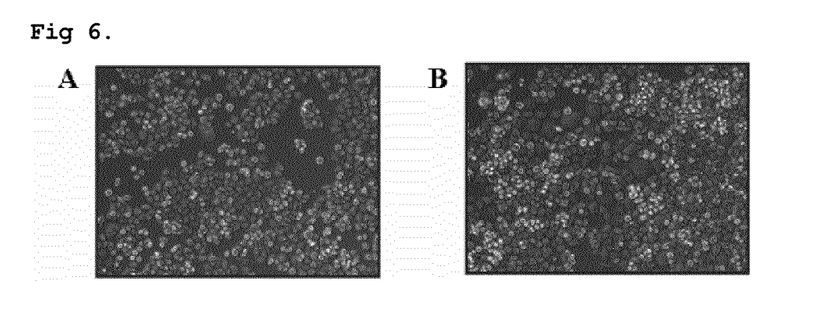
FIG. 6 shows stable blasticidin-resistant C33A cells having the HPV16 E6 reference strain (A) and the E6 variant strain (B) constructed in accordance with a preferred embodiment.

C33A cells ($5 \times 10^5$) to be constructed to express the oncogene are infected with approximately $4 \times 10^6$ TU/ml of lentivirus stock obtained by transfecting 293FT cells with pDH085 and pDH086. The lentivirus containing oncogene E6 is added to the C33A cells. In this embodiment, C33A is used as a uterine cancer cell line but CaSki, SiHa, HeLa, HeLaS3, HT3, etc. may be used. Polybrene is added in an amount of 10 μg/ml and the cells are cultured in a medium containing blasticidin (10 μg/ml) in a 37° C., 5% $CO_2$ incubator. While the medium is exchanged at an interval of 3-4 days, the cells well-cultured to have blasticidin resistance are diluted in a 96-well plate in such a manner that one cell is pipetted per well. The cells are cultured continuously until 80% of the 96-well is filled, and then are transferred to a 75 T flask to culture them until a cell count capable of extraction of DNA and RNA is obtained (FIG. 6).

Example 5

Determination of Oncogene Insertion into Genomes of Constructed Cell Line

Figure 7:
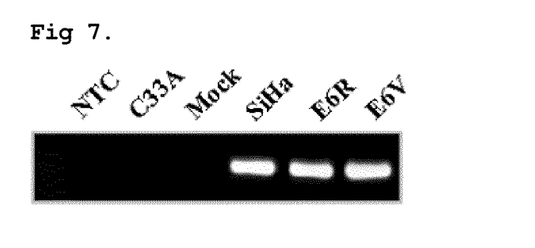
FIG. 7 shows the results of the integration of E6 genes into C33A cells, determined by PCR, wherein NTC means 'no template', C33A represents a negative control, Mock represents a control, SiHa represents a positive control, E6R represents the E6R reference strain, and E6V represents the E6 variant strain.

In a medium containing MEM-alpha, 5% FBS and 1% penicillin-streptomycin, the cell line constructed as described above is cultured until 80% of the 75T flask is filled and then the cells are harvested. The cells are subject to genome DNA extraction by using a QIAGEN® blood mini kit. Then, PCR is carried out under the same condition as in the case of acquisition of oncoprotein using E6-081 (Seq. No. 2)/E6-082 (Seq. No. 3) primer set in the presence of the extracted DNA as a template. After the PCR product is run through an agarose gel, a DNA band corresponding to the size of E6 gene is observed, which demonstrates that E6 gene is inserted into the genome of the host cells (FIG. 7). In addition, the base sequence is determined by sequencing analysis. The stable cell line that expresses oncoprotein E6 of the human papillomavirus type 16 variant strain constructed in accordance with an embodiment of the present invention is deposited to KCLRF (Korean Cell Line Research foundation) (Deposited Cell Line Name: HOE6V, Deposition No.: KCLRF-BP-00218, deposited on Nov. 28, 2009).

Example 6

Figure 8A:
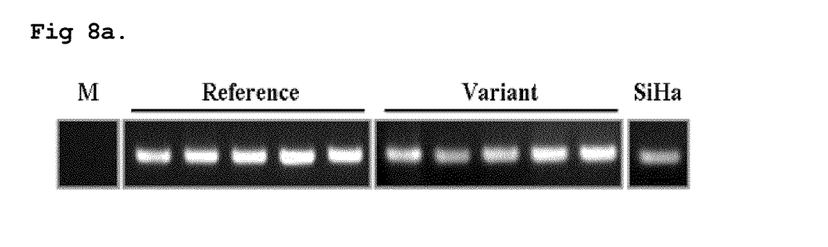
FIG. 8a shows the results of determination of E6 mRNA expression in C33A cells by RT-PCR, after the stable transfection with E6 genes, wherein M represents Mock (control)

Determination of Expression of Oncogene 6-1. Determination of Transcript Through RT-PCR In a medium containing MEM-alpha, 5% FBS and 1% penicillin-streptomycin, the cell line constructed as described above is cultured until 80% of the 75T flask is filled and then the cells are harvested. RNA is extracted by using a QIAGEN® RNase mini kit and the concentration of RNA is measured by using Invitrogen™ Qubit®. Then, cDNA synthesis is carried out by using Omniscript® reverse transcriptase (Invitrogen™) and the composition thereof is as follows: 1XRT buffer, 2 mM dNTP, 1 µM OlgiT primer, 10 units of RNase inhibitor, 4 units of Omniscript® reverse transcriptase and 2 µg of RNA. PCR is carried out by using E6-083 (Seq. No. 4)/E6-082 (Seq. No. 3) primer set in the presence of the resultant cDNA as a template under the following conditions: 1 cycle for 5 minutes at 95° C.; 30 cycles of 1 minute at 95° C., 1 minute at 60° C. and 1.5 minutes at 94° C.; 1 cycle for 10 minutes at 72° C. The PCR product is run through an agarose gel to determine the size of the amplified DNA. As a result, it can be seen from the presence of a DNA band corresponding to the expected size, 0.2 kb that transcription is performed from the E6 gene inserted into the host cells and mRNA is expressed (FIG. 8A).

6-2. Determination of Protein Expression Through Immunoprecipitation

Figure 8B:
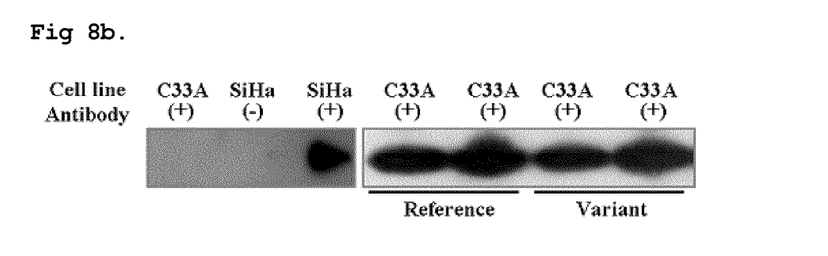
FIG. 8b shows the results of determination of E6 protein expression in C33A cells by immunoprecipitation assay, after the stable transfection with E6 genes, wherein SiHa represents a positive control.

First, protein is extracted from the cells cultured to a cell count of $1\times10^7$ in a 75T flask by using RIPA buffer. The protein concentration is measured by using Nano-Drop (Health care BioScience). Next, 60 µg of the protein is subjected to O/N reaction with 1 µg of a primary antibody against E6 at 4° C. Then, 80 µl of Puredown Protein A-Agarose is added thereto to perform a reaction at 4° C. for 4 hours. The reaction mixture is washed with PBS three times and is subjected to centrifugal separation under 1,400 rpm for 15 minutes. Then, the supernatant is removed. Nupage® LDS sample buffer and Nupage® sample reducing agent are added, the resultant mixture is boiled at 100° C. for 5 minutes and is settled down for 15 minutes, and the supernatant is taken. After that, 20 µl of the supernatant is loaded to NuPAGE® 12% Bis-Tris Gel 1.0 mm (Invitrogen™) and is run therethrough at 200V for 1.5 hours. After the running, protein is transferred to a PVDF membrane by using 1 L of 1× NuPAGE® transfer buffer to which methanol is added to a concentration of 20%. Herein, the transfer is performed at 30V for 1.5 hours. The protein-transferred membrane is blocked with TBST buffer containing 5% BSA and is allowed to react with E6 antibody (SantaCruz BioScience) in the same buffer. After the completion of the reaction, insufficiently reacted antibodies are removed from the membrane with TBST buffer containing 5% BSA and are allowed to react with anti-goat secondary antibody to detect the protein reacted with the antibody. After the reaction, the membrane is exposed to WEST-ZOL® Plus (Intron) and the expression of target protein is determined. As a result, E6 proteins corresponding to the reference strain and variant strain are detected from the cells reacted with E6 antibody. This demonstrates that the oncoprotein is expressed from the cells constructed as described above (FIG. 8B).

Example 7

Investigation of Degradation of p53 Caused by Oncogene

Figure 9:
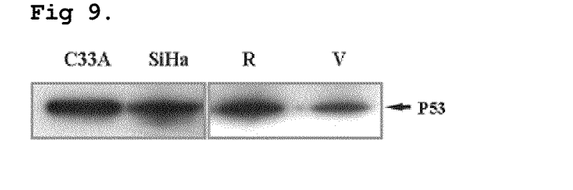
FIG. 9 shows a decrease in p53 expression caused by E6 protein of the HPV16 variant strain, as determined by western blotting, wherein R represents the E6 reference strain and V represents the E6 variant strain.

In this example, a difference in amount of protein expression between E6 protein of the reference strain and that of the variant strain is determined for p53, a tumor suppressor gene known to cause tumor genesis through the degradation thereof caused by HPV16 E6 genes. In a 75 T flask, protein is extracted from the cells cultured to a cell count of $1\times10^7$ by using RIPA buffer. The protein concentration is measured by using Nano-Drop (Health care BioScience). Next, 30 µg of the protein is loaded to NuPACE® 12% Bis-Tris Gel 1.0 mm (Invitrogen) and is run therethrough at 200V for 1.5 hours. After the running, protein is transferred to a PVDF membrane by using 1 L of 1× NuPAGE® transfer buffer to which methanol is added to a concentration of 20%. Herein, the transfer is performed at 30V for 1.5 hours. The protein-transferred membrane is blocked with TBST buffer containing 5% BSA and is allowed to react with p53 antibody (SantaCruz BioScience) in the same buffer. After the completion of the reaction, insufficiently reacted antibodies are removed from the membrane with TBST buffer containing 5% BSA and are allowed to react with anti-goat secondary antibody to detect the protein reacted with the antibody. After the reaction, the membrane is exposed to WEST-ZOL® Plus (Intron) and the expression of target protein is determined. As a result, stronger degradation of p53 is observed in the case of the variant strain E6 (FIG. 9). This suggests that tumor genesis caused by the variant strain differs from that caused by the reference strain. Therefore, it is possible to determine a difference in amounts of p53 expression between E6 protein of the human papillomavirus type 16 reference strain and E6 protein of the variant strain by using the cell line that expresses oncoprotein E6 of the human papillomavirus type 16 variant strain, thereby screening an anticancer compound of uterine cervical cancer, etc.

Example 8

Kit for Diagnosis of Uterine Cervical Cancer Using Inventive Primer Set

The primer set of Seq. No. 2/Seq. No. 3 or Seq. No. 4/Seq. No. 3 is used to amplify E6 genes of the human papillomavirus type 16 variant strain known to cause uterine cervical cancer.

In this example, an intrauterine swab is used as a test sample, wherein the intrauterine swab is obtained from a woman who engages in a class of jobs requiring examination of sexually transmitted diseases in the health center after her agreement. The DNA extracted from the sample is used as a template and PCR is carried out by using the primer set to amplify variant protein E6 of HPV16. The PCR product is subjected to agarose gel electrophoresis. In addition, the PCR product is sequenced to determine the site of base mutation.

Therefore, the primer set according to an embodiment of the present invention efficiently detects E6 genes of the human papillomavirus type 16 variant strain, and thus may be used as a kit for diagnosis of uterine cervical cancer.

While the invention has been described with respect to the specific embodiments, it will be apparent to those skilled in the art that various changes and modifications may be made without departing from the spirit and scope of the invention as defined in the following claims.

What is claimed is:

1. A cell line that expresses the protein of SEQ ID NO:1; wherein the cell type is selected from the group consisting of C33A, CaSki, SiHa, HeLa, HeLaS3, and HT3 and wherein the cell line comprises genes encoding the protein of SEQ ID NO:1.

2. The cell line as claimed in claim 1, wherein the genes are obtained by carrying out PCR (polymerase chain reaction) with primers of SEQ ID NO:2 and SEQ ID NO:3.

3. The cell line as claimed in claim 1, wherein the cell type is C33A.

4. A cell line designated HOE6V having a Korean Cell Line Research Foundation (KCLRF) Deposition No. KCLRF-BP-00218.

* * * * *

```
                              SEQUENCE LISTING

<160> NUMBER OF SEQ ID NOS: 4

<210> SEQ ID NO 1
<211> LENGTH: 151
<212> TYPE: PRT
<213> ORGANISM: Human papillomavirus type 16
<220> FEATURE:
<221> NAME/KEY: VARIANT
<222> LOCATION: (25)

<400> SEQUENCE: 1

Met Phe Gln Asp Pro Gln Glu Arg Pro Arg Lys Leu Pro Gln Leu Cys
  1               5                  10                  15

Thr Glu Leu Gln Thr Thr Ile His Glu Ile Ile Leu Glu Cys Val Tyr
             20                  25                  30

Cys Lys Gln Gln Leu Leu Arg Arg Glu Val Tyr Asp Phe Ala Phe Arg
         35                  40                  45

Asp Leu Cys Ile Val Tyr Arg Asp Gly Asn Pro Tyr Ala Val Cys Asp
     50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
             85                   90                  95

Cys Asp Leu Leu Ile Arg Cys Ile Asn Cys Gln Lys Pro Leu Cys Pro
           100                  105                 110

Glu Glu Lys Gln Arg His Leu Asp Lys Lys Gln Arg Phe His Asn Ile
         115                 120                 125

Arg Gly Arg Trp Thr Gly Arg Cys Met Ser Cys Cys Arg Ser Ser Arg
     130                 135                 140

Thr Arg Arg Glu Thr Gln Leu
145                 150

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
gttatggtta tgcaccaaaa gagaactgca atg                                33

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
ggcagctggg tttctctacg tgttc                                         25

<210> SEQ ID NO 4
<211> LENGTH: 26
<212> TYPE: DNA
<213> ORGANISM: Artificial Sequence
```

```
<220> FEATURE:
<223> OTHER INFORMATION: Primer

<400> SEQUENCE: 4
ccgttgtgtg atttgttaat taggtg                                              26
```